(12) United States Patent
Lentfer

(10) Patent No.: US 6,831,962 B2
(45) Date of Patent: Dec. 14, 2004

(54) AUTOMATIC ADJUSTING METHOD FOR A GONIOMETER AND ASSOCIATED DEVICE

(75) Inventor: Arno Lentfer, Hamburg (DE)

(73) Assignee: X-Ray Research GmbH, Norderstedt (DE)

( * ) Notice: Subject to any disclaimer, the term of this patent is extended or adjusted under 35 U.S.C. 154(b) by 61 days.

(21) Appl. No.: 10/264,773

(22) Filed: Oct. 4, 2002

(65) Prior Publication Data

US 2003/0068010 A1 Apr. 10, 2003

(30) Foreign Application Priority Data

Oct. 4, 2001 (DE) .......................................... 101 49 171

(51) Int. Cl.[7] ............................................. G01N 23/20
(52) U.S. Cl. .......................................... 378/81; 378/205
(58) Field of Search .............................. 378/70, 71, 79, 378/81, 205, 207, 80, 208

(56) References Cited

U.S. PATENT DOCUMENTS

| | | | | |
|---|---|---|---|---|
| 5,359,640 A | * | 10/1994 | Fink et al. ..................... | 378/79 |
| 5,475,218 A | | 12/1995 | Kakibayashi et al. | |
| 6,404,849 B1 | * | 6/2002 | Olson et al. .................. | 378/79 |

FOREIGN PATENT DOCUMENTS

| | | |
|---|---|---|
| WO | WO 00/40952 | 7/2000 |
| WO | WO 01/11345 A2 | 2/2001 |

OTHER PUBLICATIONS

Harting, M and Willutzki, P, "A New Method to Position a Sample on a Rotating Axis Accurately", 8056 Measurement Science and Technology 6(1995) Mar., pp. 276–280, No. 3, Bristol, GB.

Serruys, W.; Van Houtte, P.; Aernoudt, E.; "A Fully Automated Method for the Alignment of X-Ray Stress–Goniometers", Journal of Strain Analysis, pp. 155–158, vol. 23, No. 3, 1988.

* cited by examiner

Primary Examiner—Edward J. Glick
Assistant Examiner—Courtney Thomas
(74) Attorney, Agent, or Firm—McCormick Paulding & Huber LLP

(57) ABSTRACT

In order to create a method for the automatic relative adjusting of the position coordinates ($x_p$, $y_p$, $z_p$) of at least one sample with respect to the center coordinates ($x_m$, $y_m$, $z_m$) of a goniometer (200) determined by the intersection point of the tilting axles ($\omega$, $\chi$, $\phi$) as well as an associated device (100) through which the construction of goniometric systems is considerably simplified and moreover the costs for multiple circle systems are considerably reduced, it is proposed that, during a variation of the sample orientation or tilting, the trajectory of the sample which is taking place, in particular the precession trajectory of the sample, can be dynamically compensated about the center coordinates ($x_m$, $y_m$, $z_m$) and the sample can be dynamically held at the measuring point, while

[a] the trajectory of the sample about the center coordinates ($x_m$, $y_m$, $z_m$) is recorded and exploited by digital image processing,

[b] correction coordinates ($x_m - x_p$, $y_m - y_p$, $z_m - z_p$) are calculated from the exploited and recorded trajectory in order to dynamically compensate the trajectory and

[c] the sample is moved according to the calculated correction coordinates ($x_m - x_p$, $y_m - y_p$, $z_m - z_p$) into at least one of the directions of translation (x, y, z) so that this translational shifting is dynamically coupled to the moving of the tilting axles ($\omega$, $\chi$, $\phi$) of the goniometer (200) determined by the variation of the sample orientation or tilting.

10 Claims, 1 Drawing Sheet

AUTOMATIC ADJUSTING METHOD FOR A GONIOMETER AND ASSOCIATED DEVICE

CROSS REFERENCE TO RELATED APPLICATION

Applicant hereby claims foreign priority under 35 U.S.C. § 119 from German Application No. 101 49 171.9 filed 4 Oct. 2001, the disclosure of which is herein incorporated by reference.

TECHNICAL FIELD

This invention relates in general to the technical field of the centering of small samples by using standardized geometries; this invention relates in particular to a method for the automatic relative adjusting of the position coordinates of at least one sample which is on a sample holder or table of a goniometer, which is to be examined by means of the goniometer, which is movable in its position in at least one direction of translation and which is rotatable about at least one tilting axle in its orientation or tilting with respect to the center coordinates of the goniometer determined by the intersection point of the tilting axles.

This invention furthermore relates to an associated device for the automatic relative adjusting of the position coordinates.

PRIOR ART

A goniometer is a component part of an X-ray diffracting device, for example of a diffraction measuring instrument or of a diffractometer as it is used for the X-ray diffraction analysis. For the X-ray diffraction analysis by means of a diffractometer, for example a crystalline structure of a substance, is analysed by radiation of the substance with an X-ray and by measuring a diffraction angle of the X-ray reflected by the substance or having passed through this substance. A goniometer is used in relation with a diffractometer for measuring a diffraction angle of the X-ray and serves for the exact positioning of the sample inside the diffractometer.

In principle, six spatial degrees of freedom are now to be granted for the positioning of the sample in the goniometer. Here, they are the translational coordinates x, y and z (according to the three spatial directions) and the three rotational coordinates Omega ($\omega$), Chi ($\chi$) and Phi ($\phi$).

The translational degrees of freedom are used to move the sample to a determined position. This being, by using X-ray diffractometers, the sample should be at any time of the measurement exactly in the X-ray in order to guarantee stable and reliable measuring results. The cross section of the X-ray corresponds in general approximately to the cross section of the sample to be examined. Thus, the translational degrees of freedom allow to adjust the sample at a predetermined location in the X-ray.

On the other hand, the rotational degrees of freedom are used in X-ray diffractometers to vary the orientation or tilting with respect to the X-ray. An eventually dynamic variation of the orientation or of the tiling within the scope of a measurement is at present still a necessary condition for interpretable measuring results.

Mechanical arrangements with these translational as well as rotational degrees of freedom are designated as goniometers. The requirement of a high stability with respect to the position in space ($\rightarrow$ translational component) by simultaneous variation of the orientation or tilting ($\rightarrow$ rotational component) results in that these systems are mechanically very complicated and also expensive. Nowadays available systems are constructed in such a way that the orientation or the tilting of the sample is realized by interpenetrating circles of revolution, whereby usually the designation Omega ($\omega$) is associated to the external circle of revolution, the designation Chi ($\chi$) to the middle circle of revolution and the designation Phi ($\phi$) to the internal circle of revolution.

According to the prior art, there is a multitude of alternatives which get along with less than three degrees of freedom with respect to the rotational orientation or tilting. The so-called Kappa ($\epsilon$) arrangements which have a few limitations with respect to the angle of rotation as well as three rotational degrees of freedom belong to these alternatives. Furthermore, so-called two circle arrangements are known which only have two axes, namely Omega ($\omega$) and Phi ($\phi$). In the course of the last centuries, uniaxial systems ($\rightarrow$ only Phi) are also more and more used which, however, have only very limited possibilities with respect to the orientation or tilting of the sample but which are used more and more often because of their simplicity of construction.

If the position of the sample in the goniometer system is to be kept maintained even during a variation of the orientation or tilting, it is absolutely necessary that the centers of the circles of revolution meet in a common point of intersection. The deviation from this common point of intersection, i.e. the offset of the axles at the point of the sample, is also designated as "sphere of confusion". Slight deviations are more complicated to construct with an increasing number of axles and result in that the costs for such a goniometer system rise strongly overproportionally with the number of the axles.

DESCRIPTION OF THE INVENTION

Aim, Solution, Advatages

Starting from the above stated disadvantages and insufficiencies, the aim of this invention is to develop a method as well as a device for the complex process of the automatic centering which considerably simplifies the construction of the goniometric systems and also considerably reduces the costs for multiple circle systems.

This aim is achieved by a method and apparatus according to the present invention.

According to the instruction of this invention, therefore the centering is no longer executed statically but dynamically. While the above described techniques of conventional type always have the three essential components translational adjusting of the center of the goniometer in the measuring point, translational centering of the sample in the center of the goniometer and rotational orientation or tilting of the sample during the measurement, according to an inventive further development of the technique of this invention, the static centering of the sample in the center of the goniometer is completely abandoned because, according to the invention, the centering is realized dynamically by translational adjustment.

In this context, the skilled in the art in the field of the goniometric measuring methods will in particular know how to appreciate that, according to the instruction of this invention, the requirement of a coincidence as precise as possible of the axles in the center of the goniometer is superfluous. According to the invention, the position of the sample can be maintained during the measurement dynamically and during any orientation or tilting variation dynamically in the measuring position.

The further advantages which can be achieved with the method as well as with the device according to this invention consist in particular in that goniometers in any configuration can be manufactured considerably smaller and cheaper (the requirement of the precise point of intersection of all orientation or tilting axles is the essential reason for the big structural shape of existing goniometers).

According to the instruction of this invention, the mechanical requirements thus are reduced to the translational adjusting of the sample in the measuring point, whereby the movements of this translational adjusting dynamically compensate the deviations of the sample position from the measuring position and whereby it does not matter if the dynamic translational adjusting moves the whole goniometer, a part thereof or only the sample, and the rotational orientation or tilting of the sample during the measurement.

If now the position of the sample is not in the center of one of the axles of rotation of the goniometer, this results, by a rotation about this axle, in a precession or wobbling movement of the sample, this means that the sample describes an orbit about the axle of rotation. If there are several axles of rotation which can eventually also move simultaneously, there can result a complex trajectory. The orientation or the tilting of the sample is however at any time independent from the translational adjusting, i.e. a location in the coordinate system of the goniometer adjustment can be associated to any point of this trajectory.

According to an advantageous embodiment of this invention, an electronic camera system is provided in order to fix this complex trajectory before the proper measurement. Thus, each measurement has in advance a specified detailed profile of orientation or tilting variations which can be run through before the measurement with an eventually increased speed, whereby the trajectory of the sample can be recorded.

According to an advantageous further embodiment, the camera system can include at least one microscope or at least one stereomicroscope. The use of a system made of two microscopes can simplify the exploitation of complex trajectories. The images of the microscope system are analysed by appropriate software and the corresponding sets of correction coordinates of the trajectory are calculated. The position of the sample can be recorded with the aid of these correction coordinates by the translational goniometer adjustment during the measurement. The precession or wobbling movement of the non-centered sample is completely compensated for during the measurement. The translational goniometer adjustement thus results in exactly the inverse translational trajectory, and the sample remains at the measuring position.

According to a further advantageous embodiment of this invention, the translation mechanism is triggered by appropriate electronics which accomplish precise trajectory control. For a precise and quick dynamic compensation of the precession or wobbling movement of the sample, according to the invention, a control mechanism between the orientation or tilting of the goniometer axles and the three translational compensation drives (in direction of the x, y and z coordinate) is necessary. In the interplay of the orientation or tilting drive and the translation drive, the sample is held at any time of the measurement at the desired measuring position, in fact independently from its orientation or tilting in the goniometer.

According to the invention, the above described technique is independent of the proper geometry of the goniometer. Other geometries such as, for example, Kappa ($\epsilon$) arrangements which also have three rotational degrees of freedom with certain limitations with respect to the angle of rotation, or so-called two-circle systems which only have two axles, namely Omega ($\omega$) and Phi ($\phi$), or even uniaxial systems can exactly follow this principle. These systems have the advantage that the trajectory is in general incomparably simpler.

In a further advantageous configuration of this invention, a simple electronic microscope can be sufficient for this since the trajectory is eventually reduced to an elliptical orbit (for two axis goniometric systems) or to an orbit (for single axis goniometric systems).

This invention finally relates to a dynamically centering goniometer which functions according to a method described above and/or which has at least one device for the automatic relative adjusting of the position coordinates described above.

Before further configurations, characteristics and advantages of this invention are explained below in more detail with the aid of an embodiment, it is necessary to note, with respect to the relevant prior art here, that different efforts are to be recorded with respect to the automation of such systems because the automatic adjusting of a goniometer to a location is a current technique known for years.

The centering of the sample is automated in the past in different ways in that the adjustment possibilities of the goniometer head are motorized and that an electronic microscope with a corresponding software delivers the necessary adjusting variables for these motors (see Karet, G.: "Pushing the limits of Lab Automation" in Drug Discovery, March 2001, 62–66 and Muchmore, S.: "Automated Crystal Mounting and Data Collection for Protein Crystallography" in Structure 8, R243–246). Here, a manual method isautomated, i.e. manual and visual operations are simulated with the aid of computers, cameras and motors.

The motivation of all these efforts is always to realize a statical centering, i.e. the sample is adjusted in its position before each measurement so that it always remains in the center of the goniometer during the measurement during a dynamic variation of the orientation or tilting. For this method, a centering must imperatively be terminated before the proper measurement. This is the case if the sample does not change its location during a variation of its orientation or tilting.

BRIEF DESCRIPTION OF THE DRAWINGS

Further configurations, characteristics and advantages of this invention will be explained below in detail with the aid of the embodiment illustrated in FIG. 1.

DESCRIPTION OF THE PREFERRED EMBODIMENTS

Figure 1:
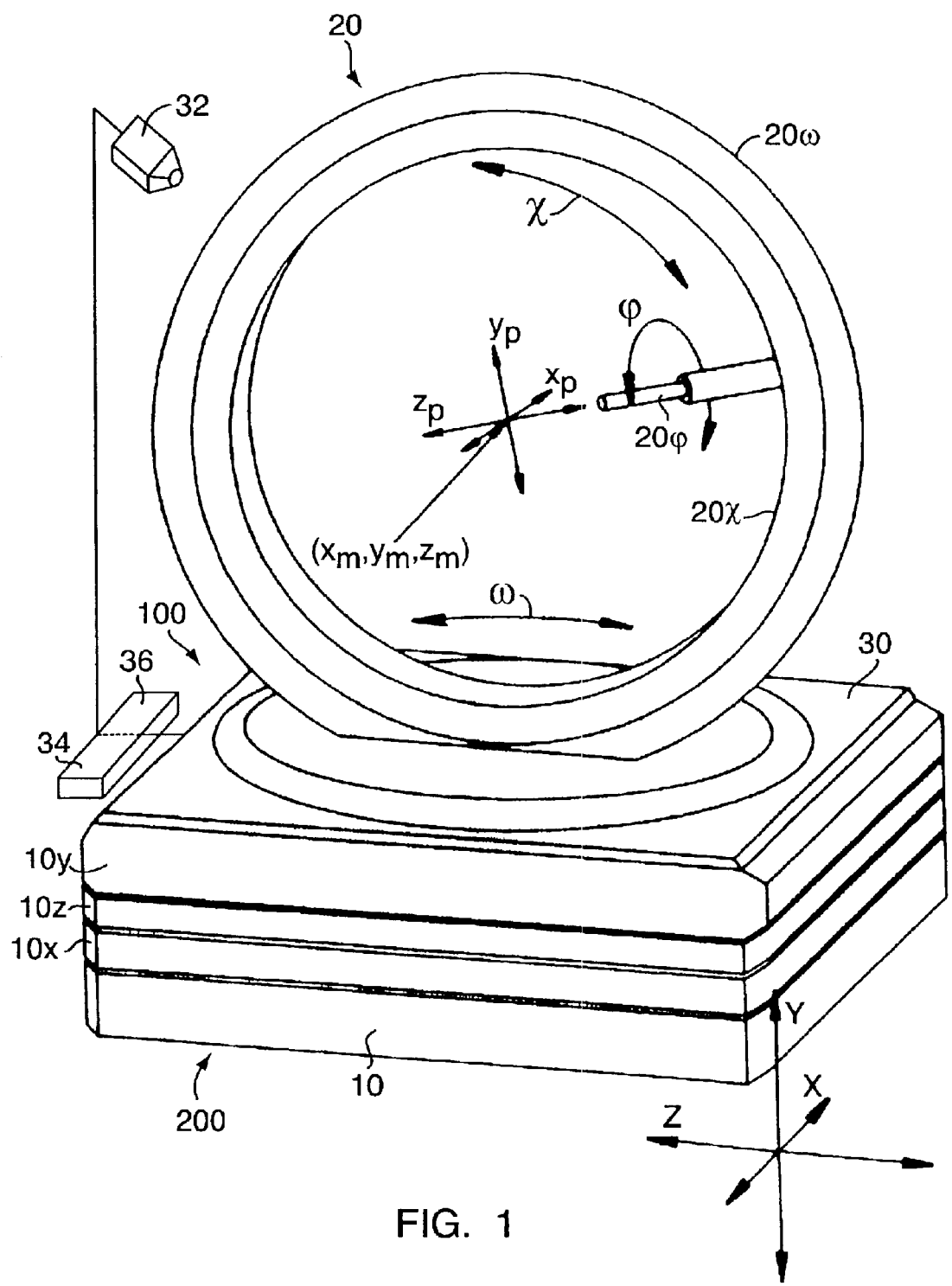
FIG. 1 shows a perspective representation of an embodiment of a goniometer with a device for the automatic relative adjusting of the position coordinates according to this invention.

For the embodiment of this invention illustrated in FIG. 1, a goniometer 200 is represented which has a device 100 for the automatic relative adjusting of the position coordinates ($x_p$, $y_p$, $z_p$) of a sample to be examined by X-ray spectroscopy by means of the goniometer 200 which is on a sample holder of the goniometer 200. Here, the automatic relative adjusting of the position coordinates ($x_p$, $y_p$, $z_p$) takes place with respect to the center coordinates ($x_m$, $y_m$, $Z_m$) determined by the point of intersection of the three tilting axles ($\omega$, $\chi$, $\phi$) of the goniometer 200.

The rotational positioning of the goniometer 200 is made by a rotation mechanism 20 which is destined for tilting the sample about the tilting axles ($\omega$, $\chi$, $\phi$) and here in particular by a rotation mechanism 20$\omega$ for the first angle coordinate $\omega$, by a rotation mechanism 20$\chi$ for the second angle coordinate $\chi$ and by a rotation mechanism 20$\phi$ for the third angle coordinate $\phi$.

The translational positioning of the goniometer 200 is made by a translation mechanism 10 placed substantially outside the rotation mechanism 20, destined for moving the position ($x_p$, $y_p$, $z_p$) of the sample in at least one direction of translation (x, y, z) and here in particular by a shifting table 10x into the first direction of translation x, by a shifting table 10y into the second direction of translation y and by a shifting table 10z into the third direction of translation z. These shifting tables 10x, 10y, 10z allow to move the goniometric system to a position ($x_p$, $y_p$, $z_p$) in the three-dimensional space (x, y, z). Consequently, the center ($x_m$, $y_m$, $z_m$) of the circles of revolution is adjusted to the measuring point by means of these three shifting tables 10x, 10y, 10z, whereby these three translational degrees of freedom (x, y, z) are placed mechanically outside the circles of revolution ($\omega$, $\chi$, $\phi$).

The sample to be examined is mounted on the inner axle Phi ($\phi$). To this purpose, this axle Phi ($\phi$) is provided at its end in the vicinity of the target position with a mounting device (which is not explicitly represented in FIG. 1 for reasons of clearness of the representation).

The sample is generally pre-assembled on a sample holder. If the sample holder is mounted on the Phi ($\phi$) axle, it is to note that the sample generally is not in the center ($x_m$, $y_m$, $z_m$) of the circles of revolution. This results in that the sample leaves the target location during a variation of the orientation or tilting ($\phi$, $\chi$, $\phi$). This is justified by inaccuracies by mounting the sample on the sample holder.

These deviations now require according to the invention a device 100 for the automatic relative adjusting of the position coordinates ($x_p$, $y_p$, $z_p$) of the sample in form of an additional adjusting means 30 which is associated with the translation mechanism 10 and the rotation mechanism 20. By means of this adjusting means 30, the precession trajectory of the sample taking place during a variation of the sample orientation or tilting can be dynamically compensated about the center coordinates ($X_m$, $y_m$, $z_m$) and the sample can in this way be dynamically held at the measuring point.

To this purpose, the adjusting means 30 has a recording means 32 for recording the trajectory of the sample about the center coordinates ($x_m$, $y_m$, $z_m$), whereby the recording means 32 is configured as an electronic camera system. Furthermore, exploitation means 34 for exploiting the recorded trajectory by digital image processing as well as calculating means 36 for calculating correction coordinates ($x_m-x_p$, $y_m-y_p$, $z_m-z_p$) from the exploited trajectory in order to dynamically compensate this trajectory are provided for. According to the representation in FIG. 1, the exploitation means 34 and the calculating means 36 are combined with an electronic control means switched between the translation mechanism 10 and the rotation mechanism 20.

According to these calculated correction coordinates ($x_m-x_p$, $y_m-y_p$, $z_m-z_p$), the sample can then be moved by means of the translation mechanism 10 in at least one of the directions of translation (x, y, z) so that this translational shifting is dynamically coupled to the moving of the tilting axles ($\omega$, $\chi$, $\phi$) of the goniometer 200 determined by the variation of the sample orientation or tilting.

In order to anticipate appropriately the relative automatic adjusting processes which must be carried out by the device 100, according to this embodiment, it can be an inventive essential part of the method to record the trajectories before the proper examination of the sample. In this context, these trajectories can then be run through with an increased speed because the proper measurements are not yet executed.

The above mentioned sample holder itself is equipped with a further translational adjusting possibility which allows an adjustment in three directions. Here also, it is a matter of a (x, y, z) adjustment, whereby this z axle is mostly configured parallel to the Phi ($\phi$) axle. This component is however constructed quite small so that it can be placed in direct vicinity of the sample. Generally, this adjusting device is designated as a goniometer head. The adjusting possibilities of this goniometer head serve for the positioning of the sample in the center of the circles of revolution. The orientation or tilting of the sample is naturally not influenced by these settings.

This so-called centering of the sample in the goniometer with the aid of the adjustable goniometer head is assisted for example by a microscope. For this purpose, the microscope is for example equipped with a cross hair which is adjusted to the center of the goniometer. The (x, y, z) adjustment in the goniometer head is varied for centering until the sample is in the center of the circles of revolution ($x_m$, $y_m$, $z_m$). The sample will also remain here by a variation of the orientation or tilting ($\omega$, $\chi$, $\phi$).

List of References

Device
Translation mechanism
  10x Translation mechanism, in particular shifting table, in first direction of translation x
  10y Translation mechanism, in particular shifting table, in second direction of translation y
  10z Translation mechanism, in particular shifting table, in third direction of translation z
Rotation mechanism
  20$\omega$ Rotation mechanism for first angle coordinate_
  20$\chi$ Rotation mechanism for second angle coordinate_
  20$\phi$ Rotation mechanism for third angle coordinate_
Adjusting means
Recording means
Exploiting means
Calculating means
Goniometer
x First direction of translation
$x_m$ First center coordinate of the goniometer 200
$x_p$ First position coordinate of the sample
y Second direction of translation
$y_m$ Second center coordinate of the goniometer 200
$y_p$ Second position coordinate of the sample
z Third direction of translation
$z_m$ Third center coordinate of the goniometer 200
$z_p$ Third position coordinate of the sample
Angle coordinate of the first tilting axle
Angle coordinate of the second tilting axle
Angle coordinate of the third tilting axle

What is claimed is:

1. A method for relative adjusting of position coordinates $(x_p, y_p, z_p)$ of at least one sample which is on a sample holder or table of a goniometer (200), which is to be examined by means of the goniometer (200), which is movable in its position $(x_p, y_p, z_p)$ in at least one direction of translation (x, y, z) and which is rotatable about at least one tilting axle ($\omega$, $\chi$, $\phi$) in its orientation or tilting with respect to the center coordinates $(x_m, y_m, z_m)$ of the goniometer (200) determined by an intersection point of the tilting axles ($\omega$, $\chi$, $\phi$), comprising the steps of:

dynamically compensating a trajectory, including a precession trajectory, of the sample which is taking place about the center coordinates $(x_m, y_m, z_m)$ during a variation of the sample orientation or tilting such that the sample is dynamically held at a measuring point;

recording and exploiting the trajectory of the sample about the center coordinates $(x_m, y_m, z_m)$ by digital processing;

calculating correction coordinates $(x_m-x_p, y_m-y_p, z_m-z_p)$ from the exploited and recorded trajectory in order to dynamically compensate the trajectory; and moving the sample according to the calculated correction coordinates $(x_m-x_p, y_m-y_p, z_m-z_p)$ into at least one of the directions of translation (x, y, z) so that this translational shifting is dynamically coupled to a movement of the tilting axles ($\omega$, $\chi$, $\phi$) of the goniometer (200) determined by the variation of the sample orientation or tilting.

2. A method according to claim 1, characterized in that the trajectory is recorded before a proper examination of the sample.

3. A method according to claim 1, characterized in that the trajectory is run through with an increased speed.

4. A device (100) for relative adjusting of position coordinates $(x_p, y_p, z_p)$ of at least one sample which is on a sample holder or table of a goniometer (200), which is to be examined by means of the goniometer (200) with respect to center coordinates $(x_m, y_m, z_m)$ of the goniometer (200) determined by an intersection point of tilting axles ($\omega$, $\chi$, $\phi$) which shows at least one translation mechanism (10) for moving the position $(x_p, y_p, z_p)$ of the sample in at least one direction of translation (x, y, z) and at least one rotation mechanism (20) for tilting the sample about at least one tilting axle ($\omega$, $\chi$, $\phi$), comprising:

at least one adjusting means (30) associated with the translation mechanism (10) and the rotation mechanism (20) such that during a variation of the sample orientation or tilting, a trajectory of the sample including a precession trajectory is dynamically compensated about the center coordinates $(x_m, y_m, z_m)$ and the sample is dynamically held at a measuring point;

the adjusting means (30) having at least one recording means (32) for recording the trajectory of the sample about the center coordinates $(x_m, y_m, z_m)$;

at least one exploitation means (34) for exploiting the recorded trajectory by digital image processing; and at least one calculating means (36) for calculating correction coordinates $(x_m-x_p, y_m-y_p, z_m-z_p)$ from the exploited trajectory in order to dynamically compensate this trajectory, and to calculate correction coordinates $(x_m-x_p, y_m-y_p, z_m-z_p)$ according to which the sample is moved by means of the translation mechanism (10) into at least one of the directions of the translation (x, y, z) so that this translational shifting is dynamically coupled to a movement of the tilting axles ($\omega$, $\chi$, $\phi$) of the goniometer (200) determined by the variation of the sample orientation or tilting.

5. A device according to claim 4, characterized in that the recording means (32) is configured as at least one electronic camera system.

6. A device according to claim 4, characterized in that the camera system is completed by at least one preferably electronic microscope or by at least one preferably electronic stereomicroscope.

7. A device according to claim 4, characterized in that the exploiting means (34) and the calculating means (36) are combined with at least one preferably electronic control means switched between the rotation mechanism (20) and the translation mechanism (10).

8. A goniometer (200) comprising:

at least one device (100) for a relative adjusting of position coordinates $(x_p, y_p, z_p)$ of at least one sample which is on a sample holder or table of the goniometer (200), which is to be examined by means of the goniometer (200) with respect to center coordinates $(x_m, y_m, z_m)$ of the goniometer (200) determined by an intersection point of tilting axles ($\omega$, $\chi$, $\phi$);

at least one translation mechanism (10) for moving the position $(x_p, y_p, z_p)$ of the sample in at least one direction of translation (x, y, z);

at least one rotation mechanism (20) for tilting the sample about at least one tilting axle ($\omega$, $\chi$, $\phi$);

at least one adjusting means (30) associated with the translation mechanism (10) and the rotation mechanism (20) such that during a variation of the sample orientation or tilting, a trajectory of the sample including a precession trajectory is dynamically compensated about the center coordinates $(x_m, y_m, z_m)$ and the sample is dynamically held at a measuring point;

the adjusting means (30) having at least one recording means (32) for recording the trajectory of the sample about the center coordinates $(x_m, y_m, z_m)$;

at least one exploitation means (34) for exploiting the recorded trajectory by digital image processing; and at least one calculating means (36) for calculating correction coordinates $(x_m-x_p, y_m-y_p, z_m-z_p)$ from the exploited trajectory in order to dynamically compensate this trajectory, and to calculate correction coordinates $(x_m-x_p, y_m-y_p, z_m-z_p)$ according to which the sample is moved by means of the translation mechanism (10) into at least one of the directions of translation (x, y, z) so that this translational shifting is dynamically coupled to a movement of the tilting axles ($\omega$, $\chi$, $\phi$) of the goniometer (200) determined by the variation of the sample orientation or tilting.

9. A goniometer according to claim 8, characterized in that the translation mechanism (10) is placed substantially outside the rotation mechanism (20).

10. A goniometer according to claim 8, characterized in that the translation mechanism (10) is placed substantially inside the rotation mechanism (20).

* * * * *